US 8,538,780 B1

(12) United States Patent
Sweeney et al.

(10) Patent No.: US 8,538,780 B1
(45) Date of Patent: Sep. 17, 2013

(54) SYSTEM FOR IDENTIFYING AND ADDRESSING CONCERNS OF MEDICAL PATIENTS

(71) Applicant: Sweeney Healthcare Enterprises, LLC, Lithia, FL (US)

(72) Inventors: Colleen Sweeney, Lithia, FL (US); Steven Widder, Lithia, FL (US)

(73) Assignee: Sweeney Healthcare Enterprises, LLC, Lithia, FL (US)

( * ) Notice: Subject to any disclaimer, the term of this patent is extended or adjusted under 35 U.S.C. 154(b) by 0 days.

(21) Appl. No.: 13/684,931

(22) Filed: Nov. 26, 2012

(51) Int. Cl.
*G06Q 50/00* (2012.01)
*G06Q 40/00* (2012.01)

(52) U.S. Cl.
USPC .................................. 705/3; 705/4

(58) Field of Classification Search
USPC ............... 706/11; 705/2–4, 7.33, 14, 14.1; 709/203, 224
See application file for complete search history.

(56) References Cited

U.S. PATENT DOCUMENTS

| 5,848,396 | A * | 12/1998 | Gerace | 705/7.33 |
| 6,009,420 | A | 12/1999 | Fagg, III et al. | |
| 6,014,630 | A * | 1/2000 | Jeacock et al. | 705/3 |
| 7,716,072 | B1 * | 5/2010 | Green et al. | 705/3 |
| 8,086,552 | B2 | 12/2011 | Randazzo et al. | |
| 8,165,898 | B2 | 4/2012 | Kalamas | |
| 8,249,924 | B1 * | 8/2012 | Mowry | 705/14.1 |
| 2003/0187733 | A1 * | 10/2003 | Hertling et al. | 705/14 |
| 2003/0195927 | A1 * | 10/2003 | Virine et al. | 709/203 |
| 2004/0220829 | A1 * | 11/2004 | Baharav et al. | 705/2 |
| 2007/0124173 | A1 * | 5/2007 | Morag et al. | 705/2 |
| 2007/0174453 | A1 * | 7/2007 | Donoho et al. | 709/224 |
| 2009/0132286 | A1 * | 5/2009 | Blaquier | 705/3 |
| 2010/0198755 | A1 * | 8/2010 | Soll et al. | 706/11 |
| 2011/0172499 | A1 * | 7/2011 | Simons-Nikolova et al. | 600/300 |
| 2012/0109686 | A1 * | 5/2012 | Higbie et al. | 705/3 |

FOREIGN PATENT DOCUMENTS

WO    WO 2011058463 A2 *   5/2011

\* cited by examiner

*Primary Examiner* — Lena Najarian
*Assistant Examiner* — Natalie A Pass
(74) *Attorney, Agent, or Firm* — Andriy Lytvyn; Smith & Hopen, P.A.

(57) ABSTRACT

A system is adapted to extract patient's demographic information and identify possible concerns the patient may be having about the upcoming medical procedure based on that information. The system accesses a database containing a plurality of candidate concerns commonly associated with the identified medical procedure and establishes their relevancy to the patient based on the patient's demographic information. The system allows patient to select relevant concerns from the presented list, and provides responses addressing those concerns. The responses are ranked based on their efficacy of alleviating concerns. The system is also adapted to communicate the information regarding the medical procedure and medical updates to the parties identified by the patient.

19 Claims, 5 Drawing Sheets

SYSTEM FOR IDENTIFYING AND ADDRESSING CONCERNS OF MEDICAL PATIENTS

FIELD OF INVENTION

This invention relates to the field of medical patient care.

BACKGROUND

Medical patients commonly experience stress and anxiety when facing an upcoming medical procedure. The sources of stress may be numerous including concerns about qualifications of medical personnel, potential risks associated with the medical procedure, length of the recovery process, possible complications, etc. Although patients are often aware of their anxiety, the exact causes for their concerns may be difficult to identify. The sources of anxiety vary greatly between different patients based on a wide array of factors, including age, sex, race, education level, socioeconomic status, prior medical history, religion, profession, place of residence, etc.

A major cause of stress for patients is due to concerns associated with how the medical procedure, hospitalization, and recovery will affect their familial, social, and business relationships. Effectively communicating concerns about a medical procedure to family and friends may prove difficult for many patients. Finding the right words to comfort one's spouse, children, parents, and friends may be even more difficult. Furthermore, a major source of stress for many patients is associated with responsibility of informing one's employer, colleagues, or clients about upcoming medical leave, the uncertainty of its duration, and providing continuous updates about the outcome of the procedure and the status of the recovery process.

Accordingly, there is a need for an automated system capable of accurately identifying concerns of a medical patient based on the patient's personal information and the nature of the upcoming procedure, helping the patient coping with these concerns, and automatically sending updates about the patient's health status to individuals selected by the patient. However, in view of the prior art considered as a whole at the time the present invention was made, it was not obvious to those of ordinary skill in the art how the limitations of the art could be overcome.

SUMMARY OF INVENTION

The long-standing but heretofore unfulfilled need for an automated system capable of accurately identifying concerns of a medical patient based on the patient's demographics and the nature of the upcoming procedure, helping the patient coping with these concerns, and automatically sending updates about the patient's health status to individuals selected by the patient is now met by a new, useful, and nonobvious invention.

The present invention authenticates a user and receives a patient's identification information. Based on this information, the system automatically extracts and categorizes that patient's demographic information, which may be obtained from public records, medical records, or a government or a private database. The invention includes a database containing an extensive list of possible concerns that patients facing the specified medical procedure commonly have. The system calculates the relevancy value for each candidate concern— the relevancy value represents the likelihood that the candidate concern is going to be relevant to the user based on the user's personal information.

In one embodiment, each candidate concern has a profile that includes a set of demographic factors relevant for that concern. The patient's personal data is compared to the profile of each candidate concern. For every characteristic that is relevant to the candidate concern, a link is established. The link is classified either as a match or a mismatch based on whether the patient's data falls within the acceptable range. Each characteristic has an associated coefficient, where the value of the coefficient represents the importance of the characteristic to the relevance of the concern. Matches result in a positive sign being assigned to the coefficient, while mismatches result in a negative sign. All coefficients are summed up to obtain the overall relevance value. The candidate concerns having the highest relevancy numbers are deemed to have the highest likelihood of being relevant to the patient.

The list of the highest ranked concerns is presented to the user, and the user selects the ones that the patient finds important. The system also comprises a database containing pre-authored answers addressing each concern. Each response has a rank based on its past efficacy of addressing the corresponding concern. The system presents the highest ranked response to the user, which the user identifies either as effective or not. If the response was effective, its rank is increased and the system moves on to the next selected concern. In case the response was not effective, the system presents the next highest ranked response on the list. The process is repeated until one of the responses effectively dispels the patient's anxiety, or the user elects to move onto the next concern.

Medical practitioners, hospitals, and various entities providing patient care will also benefit from the present invention. One of the main objectives of the invention is identifying and alleviating patients' concerns to ensure that patients feel comforted. Achieving this objective would significantly improve patients' overall experience, which will very likely correspond to higher survey scores for the medical entity. In the modern environment, prospective patients usually do extensive research prior to selecting a healthcare provider, and survey scores constitute one of the factors that many patients heavily rely upon. Consequentially, high survey scores may significantly increase an appeal of a medical entity and may be utilized as a powerful marketing tool to attract new patients.

Furthermore, correct identification of patients' concerns based on their demographic information may have significant marketing implications for a myriad of businesses associated with medically-related products and services. The present invention may help to identify patients who may benefit from a particular product or service, thus creating excellent opportunities for effective personalized marketing.

The present invention also has a functionality of addressing patients' concerns associated with communicating the news about their medical procedure to their social and business circles. The system allows the user to identify the parties whom the user wishes to inform about the upcoming procedure. The user may classify each party by selecting a predefined classification. The system comprises a database containing template messages corresponding to the medical procedure. The system selects a template message corresponding to the party's classification and customizes the message with the patient's and the party's information to give the message a personalized appearance. The customized message is presented to the user so that she can review and edit the message if necessary. The message is then electronically sent to the intended party. The user may also select an option of providing updates about the progress of the medical procedure and patient's status to the selected parties. The system periodically accesses the patient's medical records to identify whether any updates have been recorded. The process of selecting and customizing a template message is repeated for each update.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The present invention provides an automated system for identifying and addressing concerns of patients facing an upcoming medical procedure. Traditionally, the patient would identify what he believes are his top concerns and communicate them to a healthcare provider. The healthcare provider would address those concerns based on her knowledge and experience. This gives rise to a wide array of problematic issues, which the current system eliminates by automating the process.

Although patients are usually aware of feeling anxiety, stress, and apprehension due to an upcoming medical procedure, they often cannot accurately identify the source of those negative feelings and thoughts. This may be very problematic because without an accurate identification of the patient's fundamental concerns, the medical personnel may be unable to effectively address the issue. Furthermore, the problem becomes even more complex when the patient's demographics and location are taken into consideration: for the same medical procedure, the concerns may vary greatly based on each patient's age, sex, weight, height, body mass index, race, education level, and other variables. It is not feasible for medical personnel to take into account all demographic variables when helping the patient to identify and dispel their fears, and consequentially, concerns of many patients are commonly ignored, misidentified, and not properly addressed.

Figure 1:
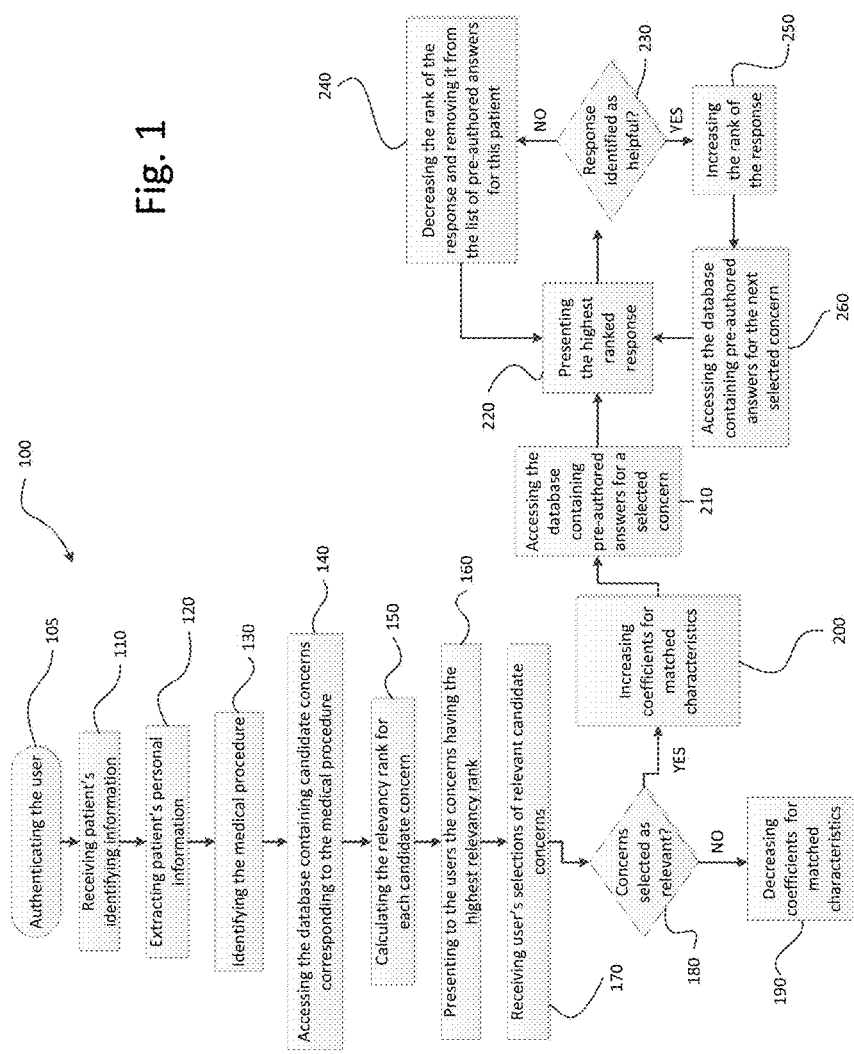
FIG. 1 is a flowchart showing an overview of the system.

System 100, as illustrated in FIG. 1, resolves this problem. System 100 utilizes capabilities of modern technology to search an extensive database of most relevant concerns commonly associated with the selected medical procedure and identifies the concerns that are likely to be of the greatest relevance to a patient based on the patient-specific demographic information.

As illustrated in FIG. 1, System 100 authenticates the user 105 and receives the patient's identification information 110. System 100 then automatically locates the hospital's records for that patient, and extracts information contained therein, including the patient's demographic factors 120, the nature of the upcoming procedure 130, and the information about the medical professional who will be performing the procedure. This automated step provides great utility by reducing the patient's stress through eliminating a necessity of repeatedly asking the patient about his demographic information, medical history, family status, etc. In most cases, such information is readily available through the hospital's records, or other database, and therefore, may be retrieved automatically without any input form the patient. Although automatic information retrieval is preferred, manual input would also work.

System 100 accesses a database 140 containing a plurality of possible concerns commonly associated with the identified procedure. The extracted patient's information is used to calculate the relevancy rank for each candidate concern 150 and to populate and present a list of most likely concerns to the user 160. The user selects the concerns that the patient identifies as relevant 170. System 100 then accesses the database containing pre-authored answers addressing each selected concern 210 and outputs the highest ranked response 220. The user relays the response the patient with the purpose of dispelling the selected concern. The user identifies whether that response was effective 230. If the presented response was not effective, system 100 will present the next highest ranked response 220. Once a helpful response has been presented, system 100 will move onto the next selected concern 260 and present the highest ranked pre-authored answer 220 corresponding to that concern. The rank of the responses identified as effective will increase 250, while the rank of the ineffective responses will decrease 240. System 100 uses the user's feedback to update the rankings of responses for subsequent users. It is contemplated that system 100 may be used in this manner by medical personnel, patients themselves, or their relatives and friends. System 100 may also be used in a variety of settings including a patient's home, a hospital, or a doctor's office.

Figure 5:
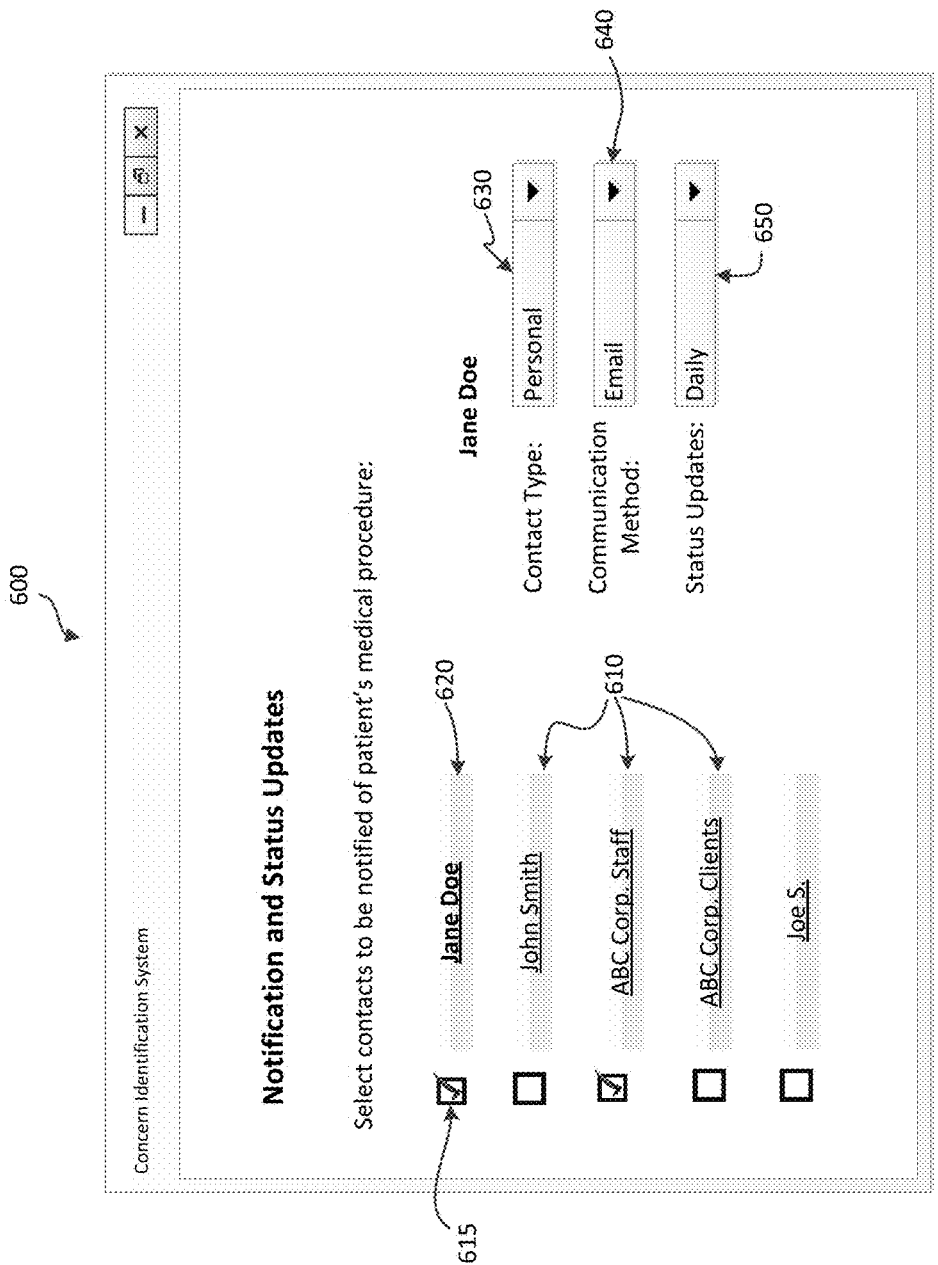
FIG. 5 is an illustration of GUI for the system, depicting a list of contacts and selection of options associated with the selected contact.

FIG. 5 illustrates a possible graphical user interface (hereinafter "GUI") 500. After system 100 obtains patient's demographic information 110 and upcoming medical procedure 130, system 100 outputs an enumerated list containing the top candidate concerns 510 for that patient. The user selects a concern 520 that is of interest to the patient. System 100 displays the highest ranked pre-authored answer 530 addressing selected concern 520. The user is given an option of either identifying that the response fully addressed selected concern 520 by clicking "YES" 540. In alternative, the user may identify the presented pre-authored answer 530 as not effective by clicking "NO" 550, which will result in the next highest ranked response being displayed. At any point, the user may click on any of the identified candidate concerns 510 to see corresponding pre-authored answers.

An important aspect of the present invention is its ability to automatically extract information about the patient without patient's direct input, thus eliminating the need to bother the patient with worrisome questions. Some of the methods for automatic information retrieval include accessing patient's medical records, using IP address to establish geographic location of the patient, and retrieving patient's information from public records or a government or private database. Some examples of the patient's personal factors that may be considered by system 100 are indicated on the following non-exhaustive list: prior medical history, age, sex, race, weight, height, body mass index, marital status, number of children, income, education level, nationality, religion, place of residence, and health insurance status. Furthermore, system 100 may have a capability of extracting relevant information about the healthcare professional, who will be performing the procedure and relaying this information to the patient to alleviate the concerns regarding the qualifications of the professional.

Figure 2:
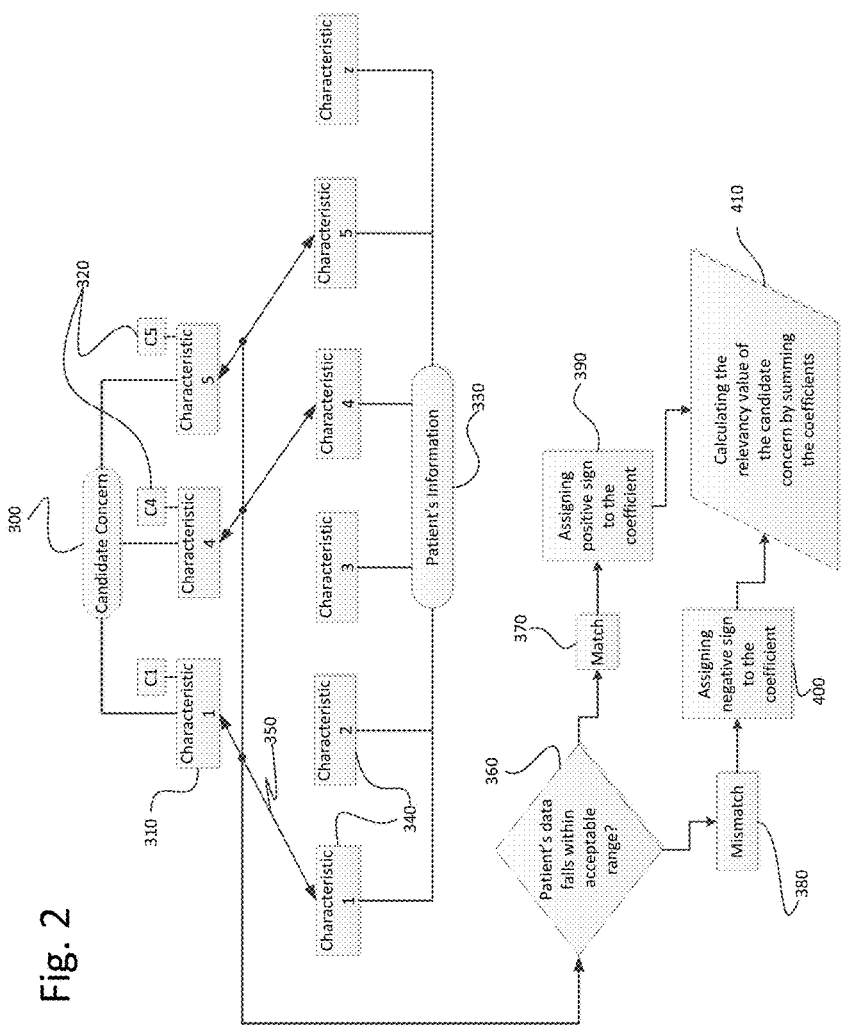
FIG. 2 is a flowchart showing an overview of the system's function of calculating relevancy values for candidate concerns.

Referring to FIG. 2, each candidate concern 300 is pre-assigned certain demographic factors 310 for which it is likely to have relevance. System 100 searches through the database and calculates the relevance value for each candidate concern. Depending on the procedure and the candidate concern, each relevant characteristic is given a coefficient 320 representing the importance that characteristic bears for the relevance of that concern.

Extracted patient's information 330 is subdivided into specific predetermined factors 340. A link 350 exists when a characteristic 340 is identified as a relevant characteristic 310 for a candidate concern 300. Every link 350 is classified either as a match 370 or mismatch 380 depending on whether the patient's data for characteristic 340 falls within the acceptable range 360 of the corresponding characteristic 310. Matches 370 result in a positive sign being assigned 390 to the corresponding coefficient 320, while mismatches 380 result in a negative sign being assigned 400 to the coefficient 320. The coefficients are summed up to obtain the total relevancy value 410 for the candidate concern.

For example, considering a case where Characteristic 1 is age, the acceptable range is over 50, and the patient's age is 43: the age characteristic will be classified as a mismatch because the patient's data for this characteristic—age 43—falls outside acceptable range—over 50, meaning that the candidate concern is unlikely to be relevant to the patient. Accordingly, since the age characteristic results in a mismatch, the coefficient for this characteristic will be assigned a negative sign. This procedure is performed for all linked factors and the coefficients are summed up to obtain the relevancy value. If the characteristic has a significant effect on the relevancy of the candidate concern, then it will have a large coefficient, meaning that a mismatch would significantly decrease the relevancy value for this concern, while a match would increase it significantly.

A person skilled in the art will appreciate that there are numerous ways of establishing the relevancy value for a candidate concern. One possible method of calculating the relevance of a candidate concern is explained below. The method is illustrated by applying each step to an example with the following facts: the patient is a married woman with 3 children residing in Florida; medical procedure is giving birth; and the candidate concern is "surviving the childbirth."

a) Each demographic characteristic is represented by a distinct variable. For example, m may represent the marital status of the patient, nc may represent the number of children the patient has, and r may represent the place of residence.
b) Each variable is assigned a numerical value based on the patient's information. For example, m may have the value of "1" for single, "2" for married, "3" for divorced, "4" for separated and so on; if a patient has no children, then 3 may be a suitable value for nc, and 1 may be a suitable value for r, since Florida is the most southern state in the continental United States.
c) Each candidate concern has certain factors associated with it. For example, a concern surviving a childbirth will likely be closely associated with the number of children (nc) the patient has, the marital status (m) may also have some relevance, while the place of residence (r) may be irrelevant.
d) Fourth, each characteristic of every candidate concern will have a pre-assigned range. For example, m=2 and nc<1.
e) Fifth, for each candidate concern, every patient's characteristic that falls within the specified range is identified—this will be considered a match. Expanding on the present example, a married woman will have a match in m, and a mismatch in nc since she has 3 children and thus falls outside of the specified range. Irrelevant factors are not considered either matches or mismatches.
f) Every match will be assigned a fixed positive value, and every mismatch will be assigned a fixed negative value, for example "1" and "−1" respectively. Based on the above example, the patient would have the following match values: 1 for m, −1 for nc, and r would be irrelevant.
g) Each candidate response has a coefficient assigned to every characteristic indicating the importance of that characteristic. For example, since the number of times the patient has given birth in her life is very important for the concern of "surviving the childbirth," the coefficient for nc may have a value of 90. Since marital status has some relevance for this concern, but considerably less than the number of children, coefficient for m may be 5.
h) The match values are multiplied by corresponding coefficients and the resulting values are summed up yielding the total relevance value. In the example above, the resulting value would be calculated as 90*(−1)+5*(1)=−85, meaning that the candidate concern of "surviving the childbirth" has very low relevance to this patient, which is consistent with what is typical for the patient who has already gone through the procedure 3 times and is not likely concerned about surviving the procedure.
i) The candidate concerns with the highest relevance numbers are deemed to be the most relevant concerns, and consequently, they are the ones presented to the patient. The patient than selects those concerns which are important to her.

Once the patients facing a particular medical procedure have selected their concerns from the list of presented concerns, the coefficients and ranges of factors are updated based on this information. For example, if out of 100 women with no children, 95 have a concern of surviving the childbirth, than the coefficient for nc would increase and the range may be expanded from nc<1 to nc<2 to test if women who are giving birth to their second child still have a fear of not surviving the procedure. If subsequently, the percentage of women who select this candidate concern decreases, system 100 will readjust its ranges and/or coefficients accordingly.

After the patient has selected a concern that resonates with her, system 100 accesses a database containing pre-authored answers corresponding to each selected concern. Every candidate concern has a corresponding list of candidate responses. Each response is assigned a ranking based on its helpfulness to previous users. For each selected concern, system 100 identifies the corresponding responses and presents them to the patient in an order of decreasing ranking. When the patient identifies a presented response as helpful, system 100 moves on to the next selected concern. However, if the response was not helpful, the patient skips to the next highest ranked response. This process continues until a patient identifies one of the responses as helpful, or decides to move on to the next concern.

If the patient cannot find a helpful response using system 100, but a comforting response is nevertheless provided from an extraneous source (a family member, a healthcare provider, a book, a website, etc.) the user of system 100 has an option to update the database by inputting the custom response. At that point the response will be added to the database and will be used as a candidate response for future patients. After each iteration, the rankings for the candidate responses are updated. The rankings are based on whether the patient identified the candidate response as helpful or not.

This feature enables system 100 to learn from the feedback provided by its users. Accordingly, as the number of users increases, system 100 becomes more accurate at identifying the sources of patients' anxieties and becomes more effective at providing comforting responses to its users. Moreover, system 100 is well adapted to making adjustments necessary to keep it up-to-date in the continuously evolving medical and social environment. For example, if a certain concern currently has relevance for a specific demographic sector, but then it becomes irrelevant in the future, the users of system 100 will not select that concern as one of importance to them, and consequentially, the relevance value of that concern will decrease and the concern will be phased out. Same is true for candidate responses.

Another aspect of system 100 is that it may be used by the patients themselves, the healthcare providers, and the patient's friends and relatives. For example, a hospital may provide its nurses with the present invention for use in a hospital setting. When a nurse encounters a patient who is feeling apprehensive or anxious about an upcoming medical procedure, the nurse would utilize system 100 to identify and address the sources of the patient's concerns.

Figure 3:
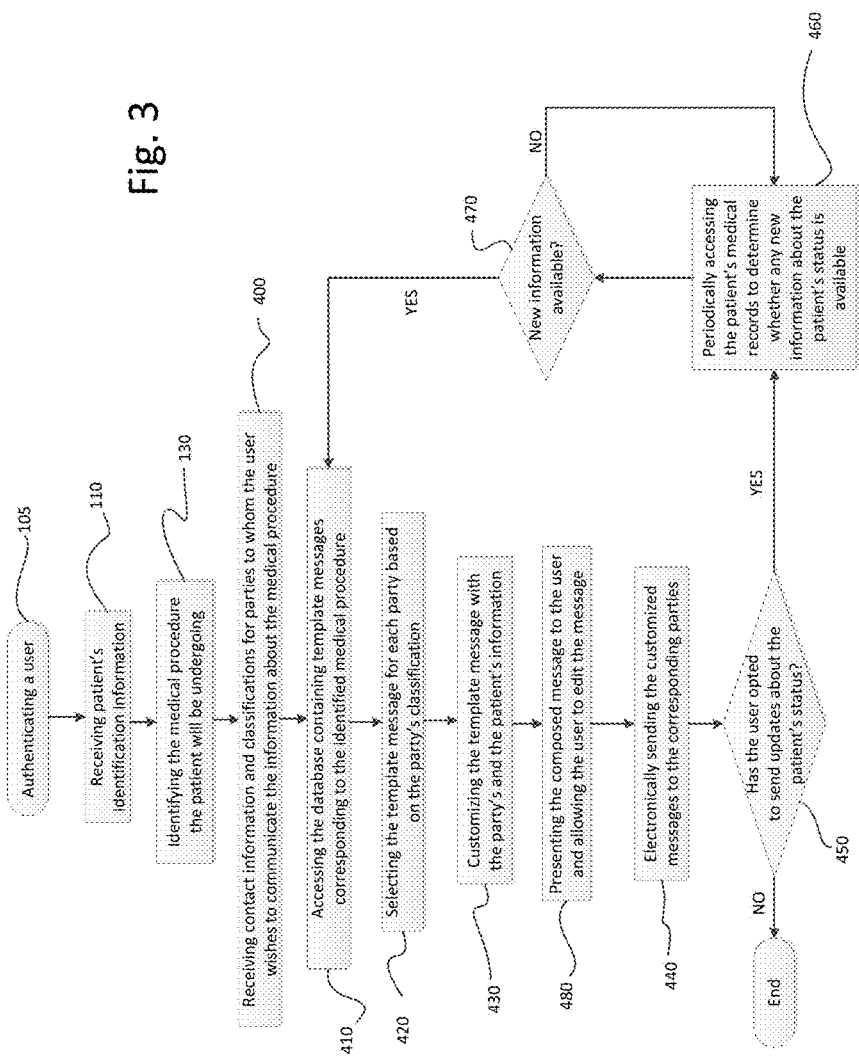
FIG. 3 is a flowchart showing an overview of the system's function of electronically sending communication messages about the medical procedure to the parties identified by the user.
Figure 4:
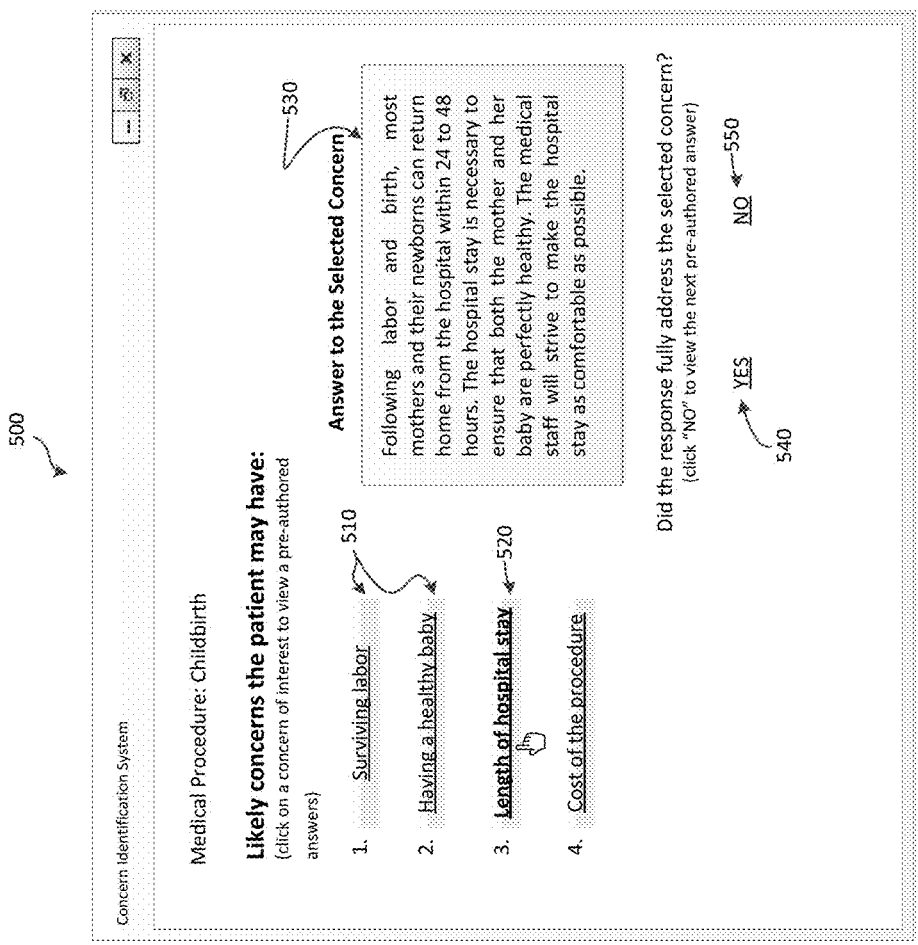
FIG. 4 is an illustration of a graphic user interface (hereinafter "GUI") for the system, depicting a list of candidate concerns and a pre-authored answer associated with the selected candidate concern.

Another feature of the present invention is illustrated in FIG. 3. According to this feature, system 100 not only identifies and addresses patients' concerns, but also automates communication between the patients and their social and business circles. One of the greatest sources of anxiety for many patients is associated with the hardship and stress placed on the patients' family members, colleagues, and employers due to the patients' inability to work and perform other tasks. Often, patients experience anxiety associated with informing their employer, colleagues, friends, and relatives of an upcoming medical leave, the risks of the procedure, and possible future complications.

The present invention reduces the stress of communicating difficult and worrisome information by automating the communication process. The system requests the user to provide contact information 400 (i.e. email, telephone number, fax number, etc.) and select one of the predefined classifications for the contact 400 (i.e. employer, friend, relative, colleague, etc.). In an alternative embodiment, the system allows the user to select contacts 400 from the user's contact list on her phone, tablet, or computer, thus requiring even less input from the user. The system then automatically generates a personalized communication message informing the selected contact that the patient will be undergoing a medical procedure and what the procedure will entail. The system accesses the template database 410, selects the appropriate templates based on the classification of contact 420 and medical procedure. The system then fills in the template with the information of the patient and addresses it to the intended addressee 430, thus giving the message a personalized appearance.

FIG. 5 illustrates an example of GUI 600 for this feature. The user is presented with a list of contacts 610. The user then selects 615 a contact 620 to be notified of the patient's upcoming medical procedure. For each selected contact 620, the user will be presented with option of identifying contact type 630, communication method 640, and frequency of patient's health status updates 650. This list of options will be presented for each selected contact.

The formality and content of the communication message will be based on selected type of contact 630. For example, a communication message for the patient's business contacts will be more formal and may contain information pertinent to the length of medical leave and whether the patient's ability to perform the work tasks will be limited during and after recovery. In contrast, a message to the patient's personal contacts may be less formal and focus more on the risks of the procedure and ways in which the friends may provide meaningful support to the patient during the pre- and post-procedure periods. The message templates to employers and colleagues are further personalized based on the patient's occupation— for example, if the patient is an attorney, the body of the message would focus on how the medical procedure may affect the patient's ability to perform mental tasks, whereas if the patient is a construction worker, the message would focus on how the procedure may affect the patient's physical health.

Moreover, referring to FIG. 3, the patient will have an option of electing to provide automatic updates 450 to selected parties about the progress of the procedure and well-being of the patient. This feature periodically accesses the medical files of the patient 460, and when new information is detected 470, a personalized message is sent to each selected contact relaying the new information. The frequency of the updates may be adjusted. The patient will also have an option of reviewing the generated messages and editing them if needed 480.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++ or the like and conventional procedural programming languages, such as the "C" programming language or similar programming languages.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

GLOSSARY OF TERMS

Candidate concern is a brief description of a pre-defined concern commonly experienced by patients facing a specified medical procedure.

Coefficient is a numerical value representing the significance of a variable with which it is associated.

Correspondence is any type of a communication message conveying certain information Demographic factors are individual pieces of demographic information. For example, age, marital status, and employment status are demographic factors.

Electronic contact list is an electronic file containing names of parties and their corresponding contact information.

Match is a correlation between patient's demographic data and demographic factors associated with a candidate concern existing only when a particular piece of patient's demographic data has relevance to the candidate concern.

Medical procedure is any diagnostic, surgical, therapeutic, rehabilitative, propaedeutic, medical practice, or any other procedure provided by healthcare practitioners or personnel.

Negative input is a user's identification of a pre-authored answer as ineffective.

Patient is a party who is likely to undergo or has undergone a medical procedure.

Patient database is a database containing information about patients of a particular medical facility, wherein each patient has a patient identifier.

Patient identified is a unique alphanumerical string that corresponds to a particular patient. The patient identifier may be assigned by the hospital, or it may be patient's social security number, name, or any other alphanumerical string unique to the patient.

Positive input is a user's identification of a pre-authored answer as effective.

Rank is a numerical value associated with a pre-authored answer indicating the likelihood that the pre-authored answer will effectively address the corresponding concern.

Relationship type is a classification of a party based on the party's relationship to the patient. Examples of contact types may include the following: personal, colleague, employer-superior, client, etc.

Relevancy value is a numerical value associated with a candidate concern indicated the likelihood that the candidate concern will be relevant to the patient.

Pre-authored answer is a text aimed at comforting the patient by addressing a concern the patient has.

Profile is a set of demographic factors associated with a specific candidate concern.

Script is a listing of discussion point relating to the medical procedure and its impact on the patient, the discussion point including a collection of pre-authored responses to patient's questions and concerns.

Template message is a pre-composed communication text having blank fields to be filled in with the information specific to a particular case and particular parties.

Third party is an individual or a collection of individuals who are not associated with the patient's healthcare provider.

User is a party operating the system.

What is claimed is:

1. One or more non-transitory tangible computer-readable media having computer-executable instructions for performing a method by running a software program on a computer, the computer operating under an operating system, the method including issuing instructions from the software program comprising:

authenticating a user through a login interface generated by the software program;

responsive to authentication, querying a patient database for a patient identifier inputted by the authenticated user, the patient identifier associated with a current patient;

querying the computer for a medical procedure linked to the patient identifier;

querying the computer for demographic information of the current patient stored in the patient database;

applying a query against a matrix of pre-authored concerns associated with the medical procedure, wherein the pre-authored concerns are based on concerns that have previously arisen in other patients undergoing the medical procedure and require no input from the current patient;

retrieving a query response that includes both a plurality of pre-authored concerns related to the medical procedure and a plurality of pre-authored answers addressing the pre-authored concerns, each pre-authored concern weighted against a plurality of demographic factors;

automatically generating a list of the pre-authored concerns from the query response, the list filtered and pre-sorted according to the demographic information of the current patient as applied to the plurality of demographic factors for each pre-authored concern retrieved from the query;

presenting the list of the pre-authored concerns to the user, wherein the list may be resorted and filtered by the user interactively;

in response to the presented list of the pre-authored concerns, confirming relevance of the presented pre-authored concerns to the current patient responsive to a user input;

presenting the pre-authored answers to the confirmed pre-authored concerns;

in response to the presented pre-authored answers, receiving the user input on whether the presented pre-authored answers have effectively addressed the concerns of the current patient; and notifying an authorized third party of an up-to-date health status of the current patient.

2. The media of claim 1, further comprising instructions to perform the steps of:

updating a rank of the presented pre-authored answers based on the user's input, wherein a positive input causes the rank to increase and a negative input causes the rank to decrease.

3. The media of claim 1, wherein the demographic information of the current patient is selected from the group consisting of prior medical history, age, sex, race, weight, height, body mass index, marital status, number of children, income, education level, nationality, religion, place of residence, employment, and health insurance status.

4. The media of claim 1, wherein the computer-readable media is selected form the group consisting of a laptop computer, a desktop computer, a mobile phone, a tablet, and a server.

5. The media of claim 1, wherein the medical procedure is a diagnostic procedure, a medical test, a therapeutic procedure, a surgical procedure, a propaedeutic procedure, or a rehabilitation procedure.

6. The media of claim 1, wherein databases containing the pre-authored concerns and the pre-authored answers are located on a centralized server, the computer accessing the centralized server via Internet.

7. The media of claim 1, wherein the user is the current patient, a healthcare provider, a member of medical personnel, a family member of the current patient, or an authorized third party.

8. The media of claim 1, further comprising instructions to perform the steps of:

receiving from the user an identification of the authorized third party to whom the current patient wishes to communicate information relevant to the medical procedure the current patient is undergoing;

accessing a database containing a plurality of template messages corresponding to the medical procedure;

selecting and customizing a template message based on the demographic information of the current patient and the identification of the authorized third party; and sending the customized template message to the authorized third party.

9. The media of claim 8, further comprising instructions to perform the steps of:

polling the current patient's medical records for a new status update;

responsive to detection of the new status update, composing a message communicating the new status update; and sending the message to the authorized third party identified by the user.

10. The media of claim 8, wherein the step of receiving from the user an identification of a third party to whom the current patient wishes to communicate information relevant to the medical procedure the current patient is undergoing, comprises the steps of:

accessing an electronic contact list of the current patient and presenting the electronic contact list to the user; and responsive to the user input, selecting the authorized third party from the electronic contact list whom the current patient wishes to inform about the medical procedure.

11. The media of claim 8, wherein content of the template message corresponds to a classification of the authorized third party to whom the message is being addressed.

12. The media of claim 8, wherein the message is sent via email, SMS, MMS, or a social networking service.

13. One or more non-transitory tangible computer-readable media having computer-executable instructions for performing a method by running a software program on a computer, the computer operating under an operating system, the method including issuing instructions from the software program comprising:

authenticating a user;

receiving an identification information of a current patient;

retrieving demographic information of the current patient by extracting the information from the current patient's medical records, public records, a private database, or a government database;

identifying a medical procedure the current patient will be undergoing;

retrieving a plurality of pre-authored concerns without requiring an input from the current patient, the pre-authored concerns based on past concerns that have arisen in other patients undergoing the medical procedure, each pre-authored concern having a profile comprising a set of relevant demographic factors;

matching the demographic information of the current patient to the demographic factors of each pre-authored concern to establish a relevancy value, the relevancy value representing a likelihood that the pre-authored concern will be relevant to the patient;

presenting to the user a predetermined number of the pre-authored concerns in an order of decreasing relevancy values;

receiving a first input from the user selecting the pre-authored concerns of relevance to the current patient;

accessing a database containing a plurality of pre-authored answers corresponding to a selected pre-authored concern, each pre-authored answer having a rank;

presenting to the user the pre-authored answers in an order of descending rank;

receiving a second input from the user on whether the presented pre-authored answer has effectively addressed the selected pre-authored concern, wherein a negative input causes the media to continue presenting pre-authored answers for the current concern; and notifying an authorized third party of an up-to-date health status of the current patient.

14. The media of claim 13, wherein each demographic characteristic associated with the pre-authored concern has a corresponding coefficient representing the weight of the demographic characteristic on the relevancy value of the pre-authored concern.

15. The media of claim 14, wherein the coefficient is assigned a positive sign if the characteristic matches the current patient's demographic information and is assigned a negative sign if the characteristic does not match the current patient's demographic information, all coefficients being summed to obtain the relevancy value for the pre-authored concern.

16. The media of claim 14, further comprising instructions to perform the steps of:
   increasing the coefficient value if the pre-authored concern is selected as relevant; and
   decreasing the coefficient value if the pre-authored concern is not selected.

17. The media of claim 13, wherein each piece of the current patient's demographic information is represented by a numerical value, each pre-authored concern having a range of acceptable values for every relevant demographic characteristic, a match is established when the numerical value of the patient's information falls within the range of the acceptable values.

18. The media of claim 13, wherein the current patient's demographic information is selected from the group consisting of prior medical history, age, sex, race, weight, height, body mass index, marital status, number of children, income, education level, nationality, religion, place of residence, employment, and health insurance status.

19. The media of claim 13, wherein the computer-readable media is selected form the group consisting of a laptop computer, a desktop computer, a mobile phone, a tablet, and a server.

* * * * *